United States Patent
Daniel

(10) Patent No.: US 9,861,481 B2
(45) Date of Patent: Jan. 9, 2018

(54) IMPLANTABLE PENILE PROSTHETIC HAVING A BASE EXPANDABLE BY LIQUID INFLATION

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 15/378,060

(22) Filed: Dec. 14, 2016

(65) Prior Publication Data

US 2017/0095334 A1    Apr. 6, 2017

Related U.S. Application Data

(63) Continuation of application No. 14/560,835, filed on Dec. 4, 2014, now Pat. No. 9,561,107.

(51) Int. Cl.
    *A61F 2/26* (2006.01)

(52) U.S. Cl.
    CPC ........ *A61F 2/26* (2013.01); *A61F 2250/0003* (2013.01); *A61F 2250/0013* (2013.01)

(58) Field of Classification Search
    CPC ....... A61F 2/26; A61B 17/04; A61B 17/3468; A61B 17/06066; A61B 2017/06052
    USPC ...................................................... 600/38–41
    See application file for complete search history.

(56) References Cited

U.S. PATENT DOCUMENTS

| | | | | |
|---|---|---|---|---|
| 4,383,525 A | * | 5/1983 | Scott | ......................... A61F 2/26 600/40 |
| 4,399,812 A | * | 8/1983 | Whitehead | ................ A61F 2/26 600/40 |
| 4,628,912 A | * | 12/1986 | Fischell | .................... A61F 2/26 600/40 |
| 8,517,916 B2 | * | 8/2013 | Ellering | ................... A61F 2/26 600/40 |

* cited by examiner

*Primary Examiner* — Samuel Gilbert
(74) *Attorney, Agent, or Firm* — Coloplast Corp., Coloplast A/S; Nick Baumann

(57) ABSTRACT

An implantable penile prosthetic has a fluid distribution manifold connected between and in fluid communication with a cylinder and a base. Both of the cylinder and the base are expandable by liquid inflation.

10 Claims, 13 Drawing Sheets

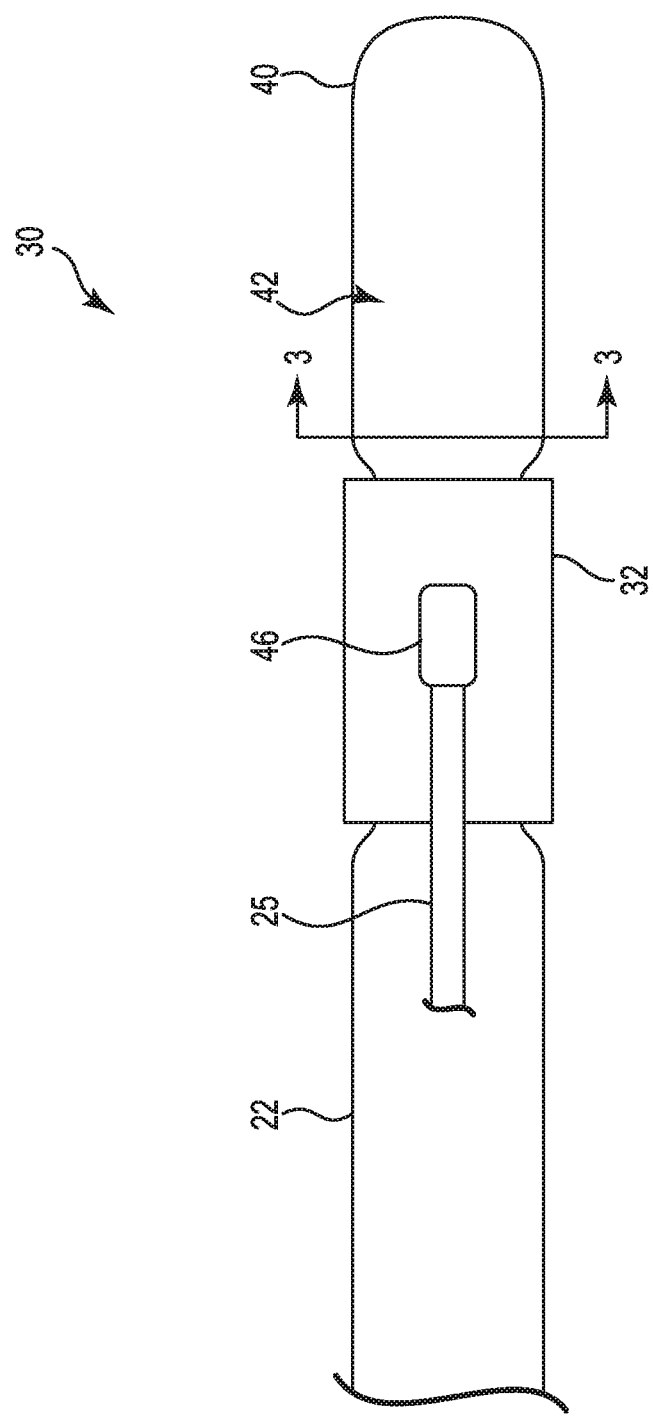

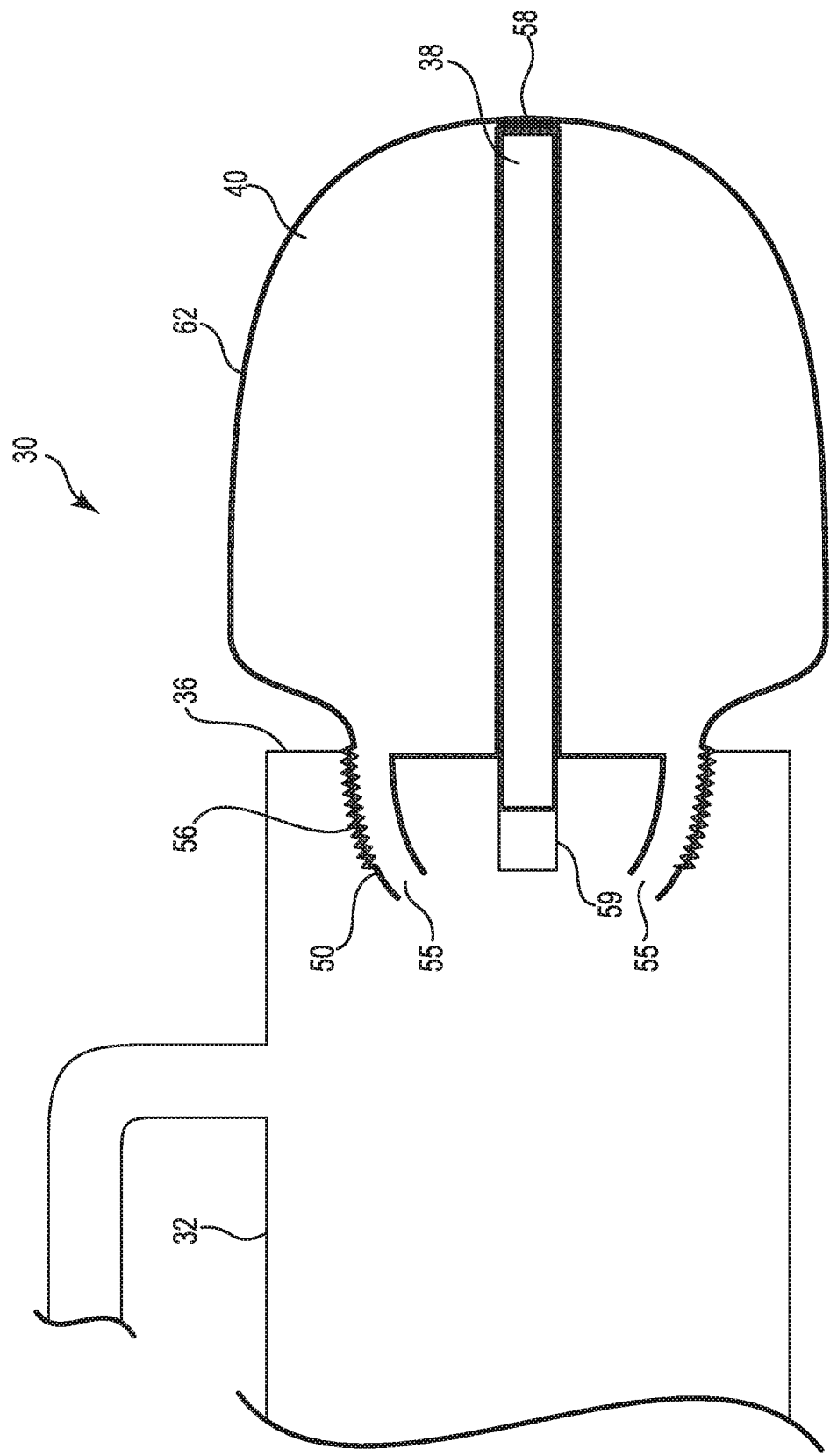

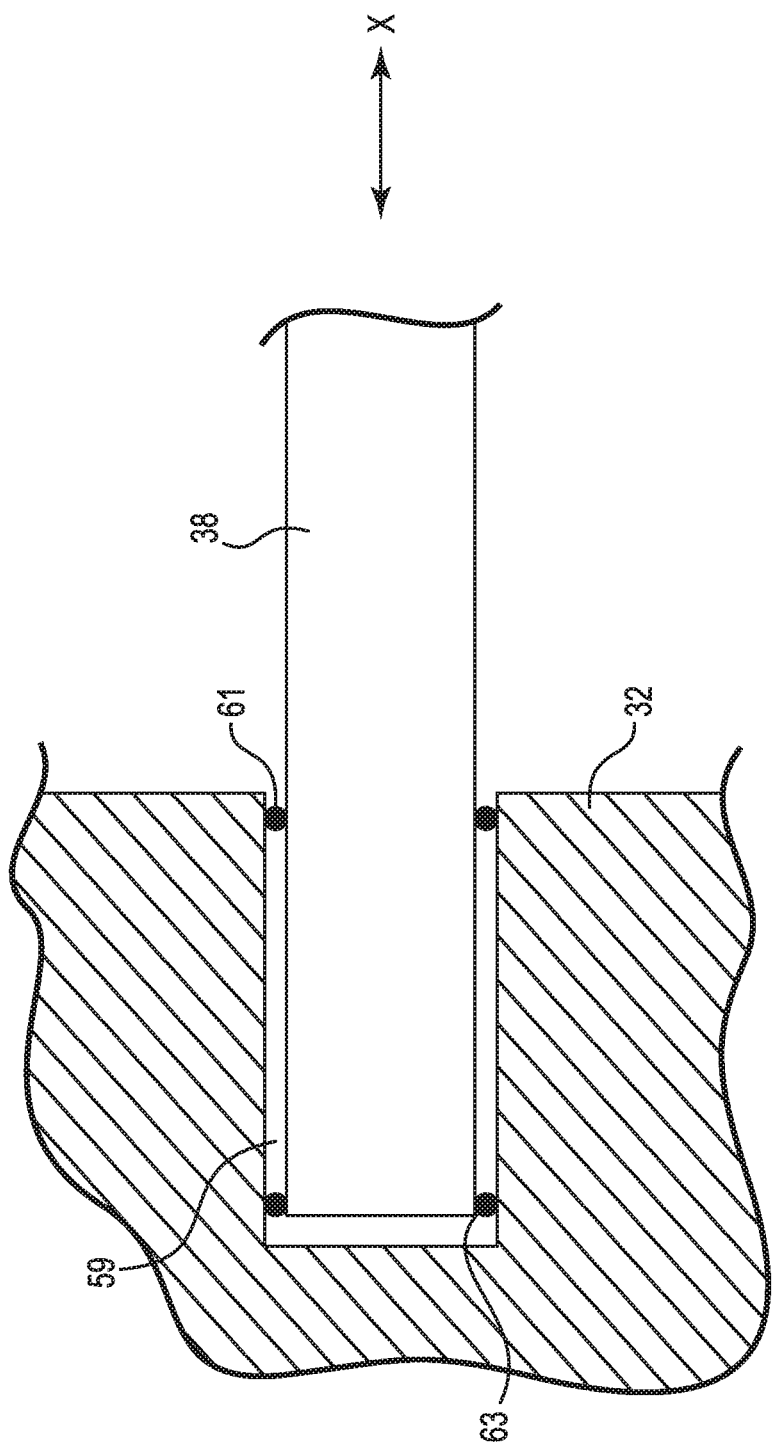

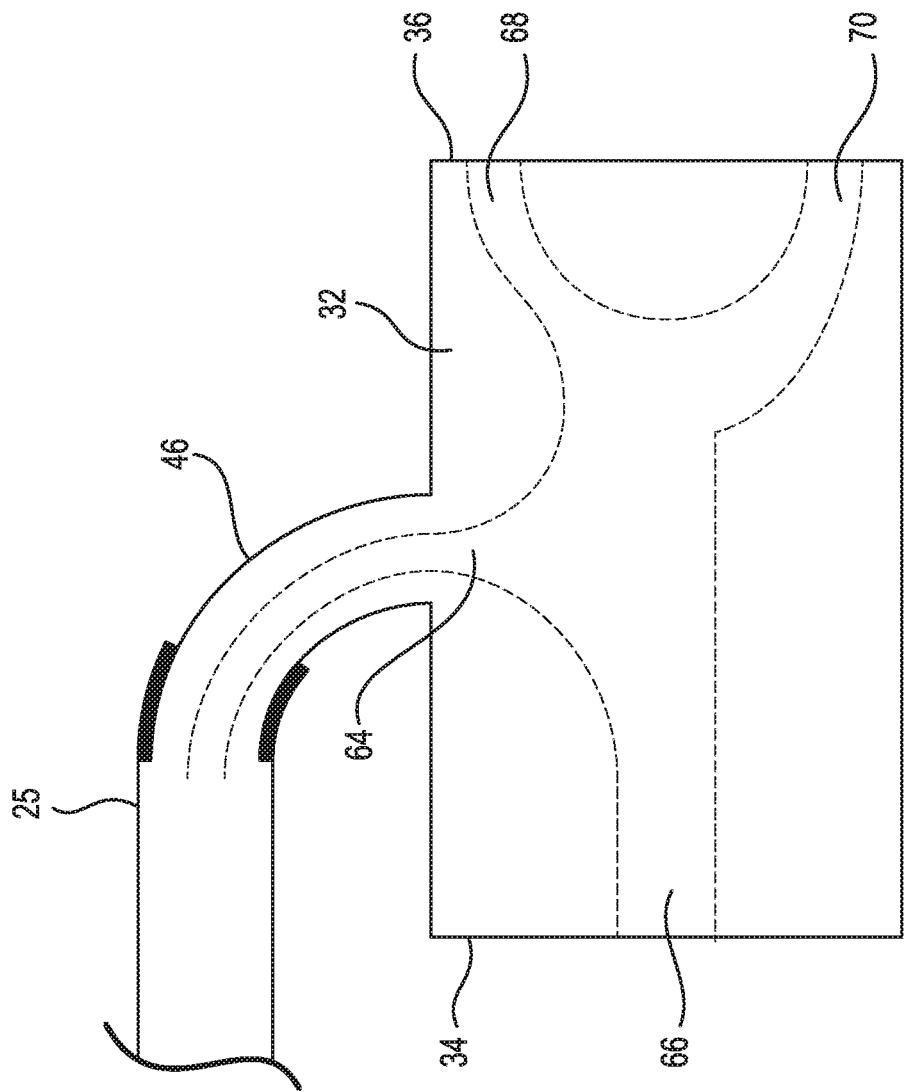

IMPLANTABLE PENILE PROSTHETIC HAVING A BASE EXPANDABLE BY LIQUID INFLATION

BACKGROUND

Penile implants provide relief for men with erectile dysfunction.

In a typical implantation procedure, the penis of the patient is incised to expose two corpora cavernosa that are aligned axially in a side-by-side orientation within the penis. A corporotomy is formed that is sized to receive the penile implant. For example, each corpora cavernosum is dilated proximally towards a crus of the penis and distally into the glans penis in a corporotomy procedure by introducing gradually larger stainless steel rods into the corpora cavernosum. The corporotomy thus has a length that extends between the crus of the penis and the glans penis. The proximal portion of the corporotomy has a diameter that is approximately the diameter of the largest stainless steel rod that the surgeon was able to insert into the corpora cavernosum. A penile implant is selected that most nearly matches the length of the corporotomy and a diameter that most nearly matches the diameter of the proximal portion of the corporotomy.

Although the above-described approach has proven effective in treating erectile dysfunction, variations in anatomy sizes require a variety of different length and diameter penile implants to be maintained in the inventory of the hospital which can be prohibitively expensive. Even with a large variety of implants available, other difficulties such as cumbersome implantation in smaller anatomies and insufficient stability of the implant in larger anatomies are still encountered by surgeons.

SUMMARY

One aspect provides a base for a penile prosthetic implant. The base includes a fluid distribution manifold having a distal end and a proximal end. The distal end of the fluid distribution manifold is attached to and in fluid communication with an inflatable cylinder sized for implantation into a corpora cavernosum of a penis. The proximal end of the fluid distribution manifold is connected to a core sized for implantation into a crus of the penis. The base further includes an inflatable bladder in fluid communication with the fluid distribution manifold. The inflatable bladder provides an outer surface of the base between a proximal end of the core and a proximal end of the fluid distribution manifold.

One aspect provides a base for a penile prosthetic implant. The base includes a distal end that is attached to and in fluid communication with an inflatable cylinder sized for implantation into a corpora cavernosum of a penis. The base includes a proximal end opposite of the distal end, the proximal end sized for insertion into a crus of the penis. The base includes a fluid port extending from a distal end portion of the base, and the fluid port communicates with a fluid distribution manifold configured to communicate with the inflatable cylinder. The base includes an inflatable bladder in fluid communication with the fluid distribution manifold and forms an exterior surface of the base. The inflatable bladder is located between the proximal end and the fluid port.

One aspect provides a penile prosthetic system including a pump, a fluid reservoir and an inflatable cylinder sized for implantation into a corpora cavernosum of a penis, the cylinder attached to a base. The base includes a fluid distribution manifold having a distal end and a proximal end. The distal end of the fluid distribution manifold is attached to the inflatable cylinder. The proximal end of the fluid distribution manifold is connected to a core sized for implantation into a crus of the penis. The base further includes an inflatable bladder in fluid communication with the fluid distribution manifold. The inflatable bladder provides an outer surface of the base between a proximal end of the core and a proximal end of the fluid distribution manifold.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2 is a top view of the embodiment of the base of FIG. 1.

FIG. 7 is a sectional side view of one embodiment of a base for a penile prosthetic implant.

FIGS. 8A and 8B are enlarged sectional side views illustrating one embodiment of a connection between parts of the base for the penile implant.

FIG. 9 is a schematic side view of one embodiment of a fluid distribution manifold.

DETAILED DESCRIPTION

Figure 1:
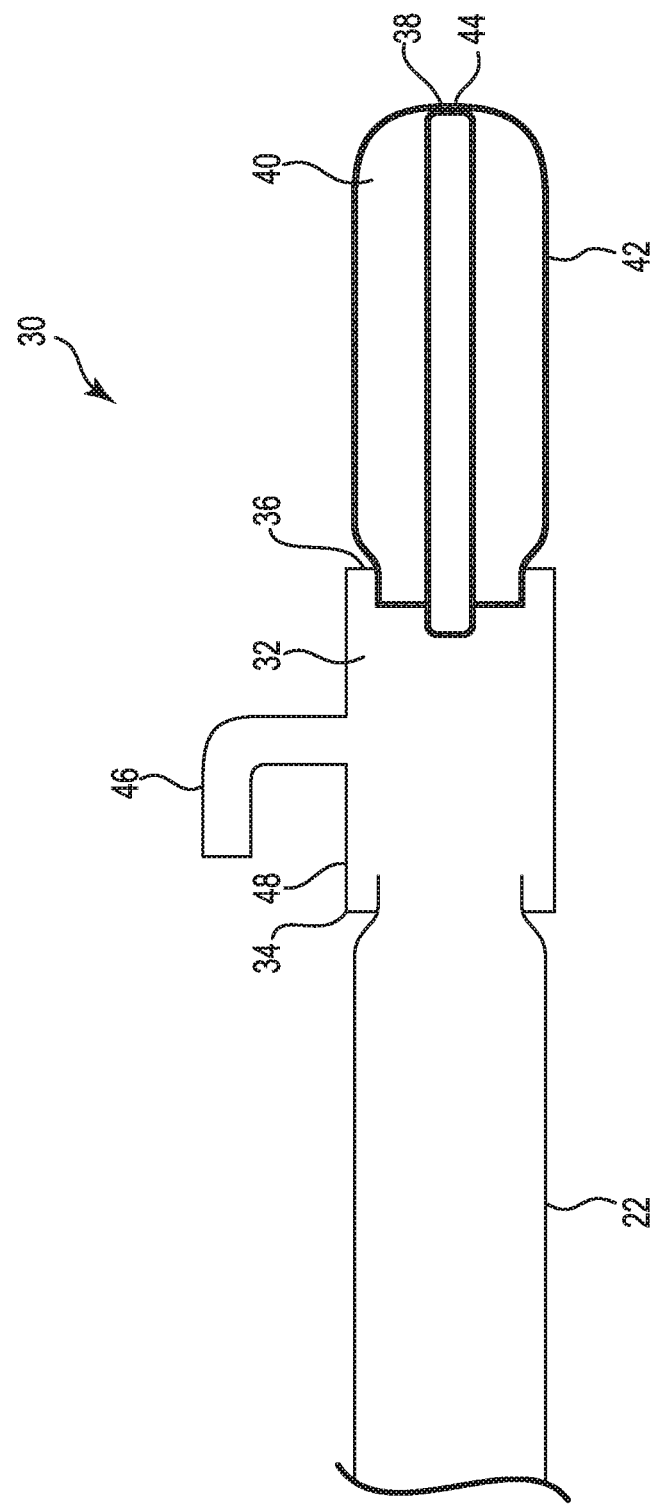
FIG. 1 is a partial cross-sectional side view of one embodiment of a base for a penile prosthetic implant.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting.

It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the crus penis of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion adjacent to the first end and another end portion adjacent to the second end.

A typical penile prosthetic implant includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir.

Different patients have different anatomy. In some patients, the anatomy of the crus of the penis is relatively small and in some cases fibrotic tissue may be present. For example, some patients will have a penile implant that requires replacement. Upon removal (explant) of the penile implant the surgeon will discover that the proximal corporotomy toward the crus of the penis has become fibrotic and difficult to open. In a patient with one or more of such characteristics, there will be less physical space in the crus of the penis thereby increasing resistance against inserting a proximal portion of a penile implant in the crus. In other patients, the anatomy of the crus of the penis is relatively large. In some cases, a larger anatomy negatively effects the stability (in the sense of capability to stay in position) of the proximal portion of the implant in the crus, which in turn may influence the stability of the cylinder part of the implant in the corpora cavernosum.

Embodiments provide a base for a penile prosthetic implant including an inflatable bladder that is transformable between a deflated state and an inflated state. During implantation of the implant, the inflatable bladder is in the deflated state which helps provide for easier insertion of a more rigid core of the base into the crus of a penis. In the use situation of the implant, i.e. when the user requires an erection, the inflatable bladder will be in the inflated state and help provide stability of the base in the crus.

Embodiments provide a base for a penile prosthetic implant that accommodates a larger variety of different sized anatomies, reduces the necessary number of inflatable cylinders of different lengths and obviates keeping stock of and using tip extenders of different diameters and length for penile implants.

FIG. 1 is a partial cross-sectional side view of one embodiment of a base 30 for a penile prosthetic implant. A fluid distribution manifold 32 includes a distal end 34 and a proximal end 36. In one embodiment, the distal end 34 of the fluid distribution manifold 32 is attached to and in fluid communication with an inflatable cylinder 22 of the penile prosthetic implant. The cylinder 22 is sized for implantation into a corpora cavernosum of a penis. In one embodiment, the proximal end 36 of the fluid distribution manifold 32 is connected to a core 38 sized for implantation into a crus of the penis. In one embodiment, the base 30 includes an inflatable bladder 40. In one embodiment, the inflatable bladder 40 is in fluid communication with the fluid distribution manifold 32. In one embodiment, the inflatable bladder 40 provides an outer surface 42 of the base 30 between a proximal end 44 of the core 38 and the proximal end 36 of the fluid distribution manifold 32. In one embodiment, the fluid distribution manifold 32 includes a fluid port 46. In one embodiment, the fluid port 46 is provided on an exterior surface 48 of the fluid distribution manifold 32 between the distal end 34 and the proximal end 36 of the fluid distribution manifold 32. In one embodiment, the core 38 includes a solid core of material.

FIG. 2 is a top view of the embodiment of the base 30 of FIG. 1. In one embodiment, the inflatable bladder 40 is provided annularly around the core 38 (in the view of FIG. 2, the core 38 is not visible through the inflatable bladder 40), although other configurations are acceptable such as having two inflatable bladders located on opposing sides, for example, of the core 38. In one embodiment, one inflatable bladder 40 is provided and the inflatable bladder 40 entirely surrounds the core 38. In one embodiment, a first end of a tubing 25 is connected with the fluid port 46 and a second end of the tubing 25 is attachable to a pump (not shown).

Figure 4:
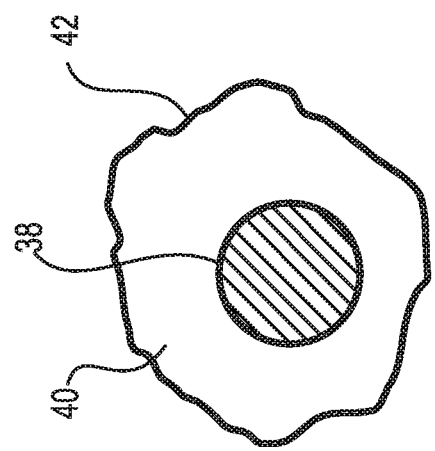
FIG. 4 is a cross-sectional view of one embodiment of an inflatable bladder in a collapsed state.
Figure 3:
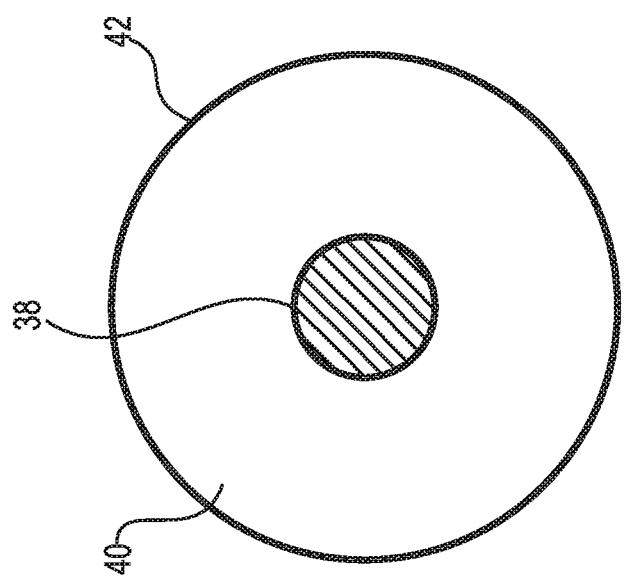
FIG. 3 is a cross-sectional view of one embodiment of a base for a penile prosthetic implant.

FIG. 3 is a cross-sectional view of one embodiment of the base illustrating the core 38 and the inflatable bladder 40 provided annularly around the core 38 as seen at a cross-section indicated by line '3-3' in FIG. 2. In one embodiment, the inflatable bladder 40 is configured to transition between a collapsed state and an expanded state. The cross-section of FIG. 3 shows one example in which the inflatable bladder 40 is in an expanded state. FIG. 4 shows a cross-sectional view of one embodiment of the inflatable bladder 40 in a collapsed state. In embodiments, an outer diameter of the inflatable bladder 40 is reduced when the inflatable bladder 40 is in the collapsed state compared to an increased outer diameter when the inflatable bladder 40 is in the expanded state. The collapsed state of the inflatable bladder is useful during implantation of the base 30 into the crus of the penis because of the reduced size of the outer diameter of the base 30 provides clearance that allows the base 30 to be inserted into narrowed or compromised crus cavities. When the penile implant is implanted and ready for use in the patient, the collapsed state of the inflatable bladder corresponds to the flaccid state of the penis. The expanded state of the inflatable bladder corresponds to the erect state of the penis when the penile implant is implanted in the patient. In large anatomies, the expanded state of the inflatable bladder is useful for providing additional stability of the base in the crus and thereby of the penile implant.

Figure 5:
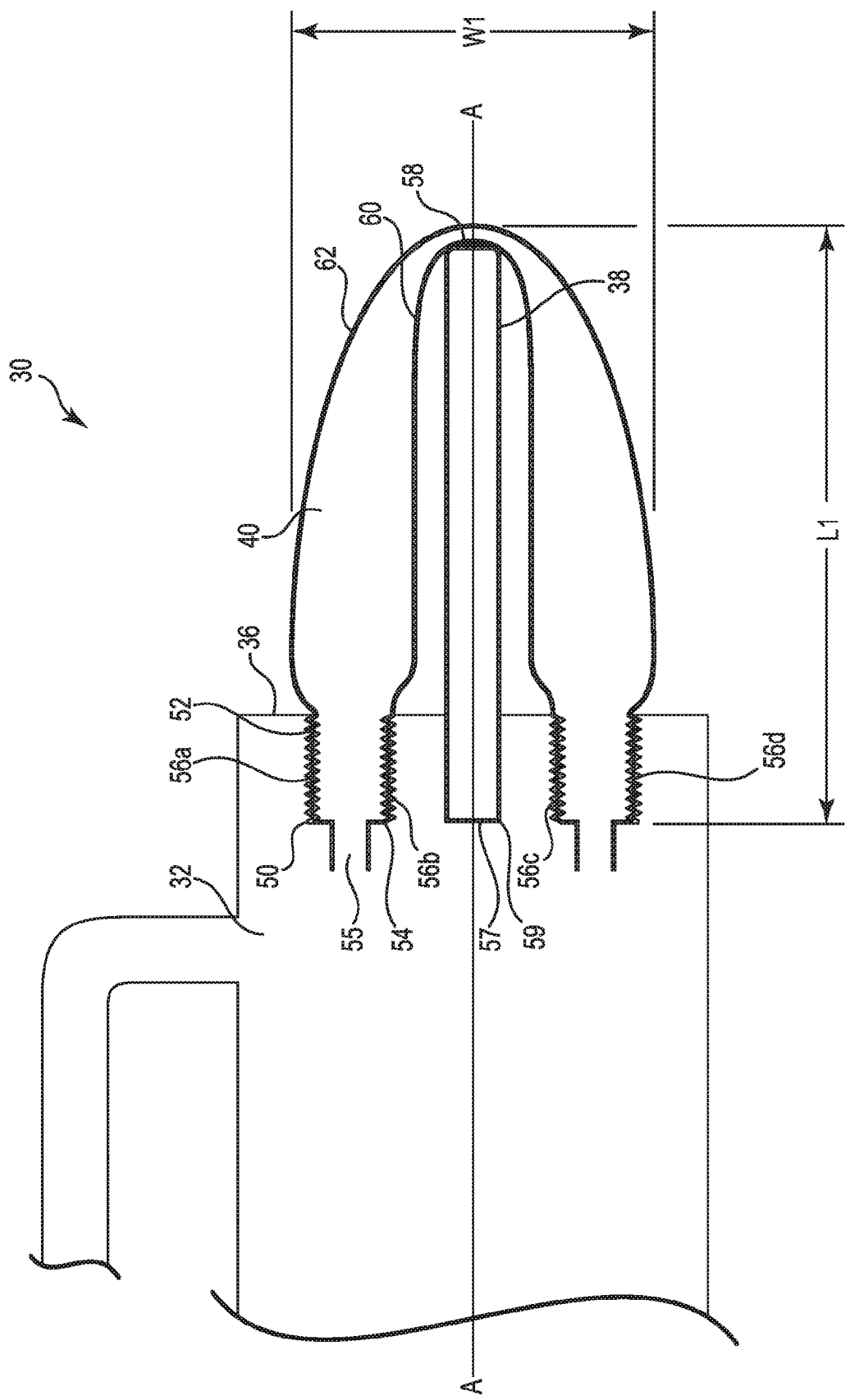
FIG. 5 is an enlarged sectional side view illustrating one embodiment of a base for a penile prosthetic implant.
Figure 6:
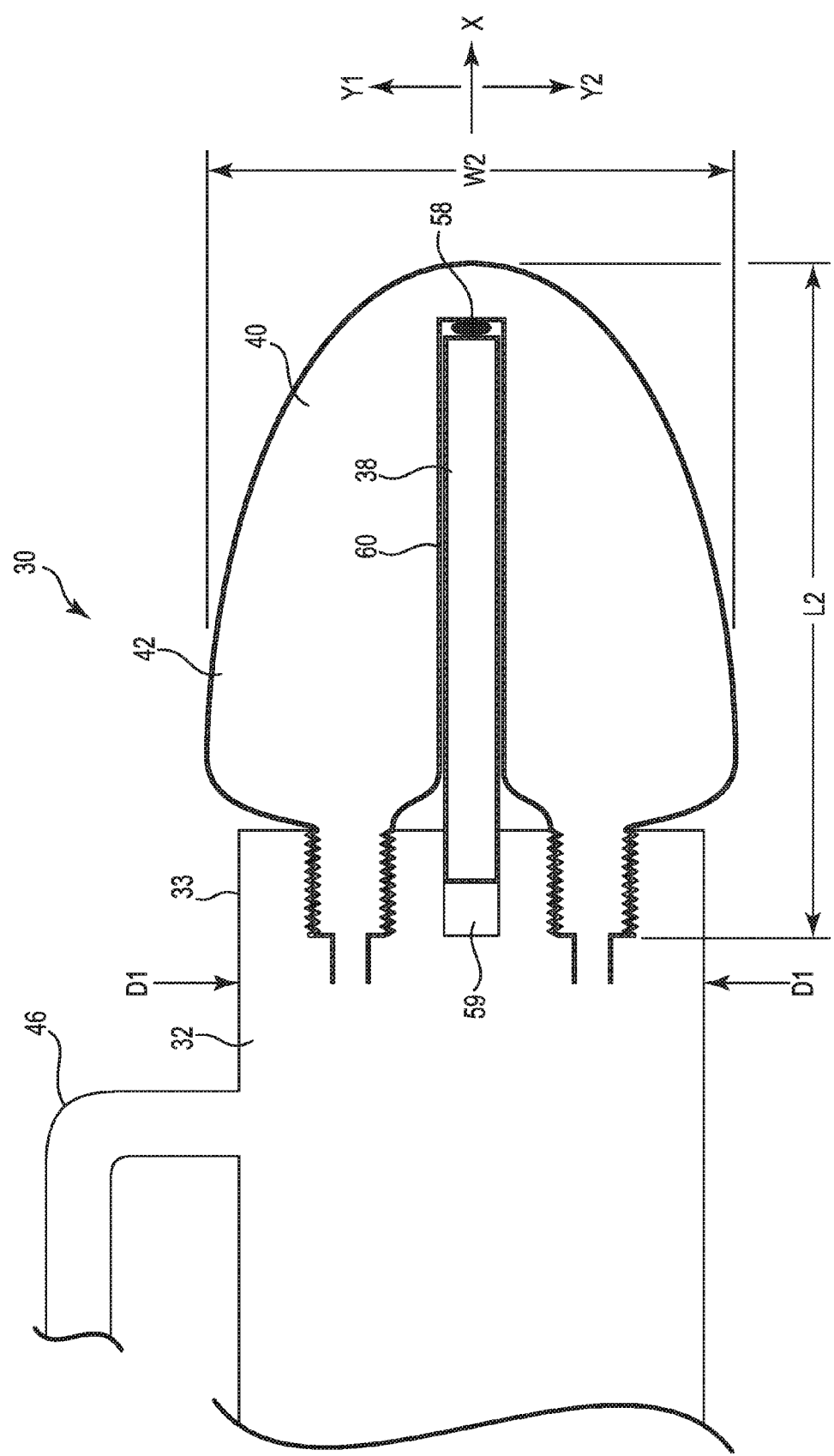
FIG. 6 is an enlarged sectional side view illustrating one embodiment of a base for a penile prosthetic implant.

FIGS. 5 and 6 are enlarged partial cross-sectional views illustrating embodiments of attachments between the inflatable bladder 40, the core 38 and the fluid distribution manifold 32. It should be noted that distances and dimensional relationships between the individual components are shown in an exaggerated manner for illustration purposes.

FIG. 5 illustrates one embodiment in which the inflatable bladder 40 is in the collapsed state. In one embodiment, the inflatable bladder 40 is attached at or adjacent the proximal end 36 of the fluid distribution manifold 32. In one embodiment, a distal end portion 50 of the inflatable bladder 40 is attached to an interior surface 52 of the fluid distribution manifold 32. In one embodiment, at least a partial section of the distal end portion 50 is attached to the fluid distribution manifold 32. In one embodiment, the distal end portion 50 of the inflatable bladder 40 is received in a pocket 54 provided in the proximal end 36 of the fluid distribution manifold 32. In one embodiment, the pocket 54 is substantially U-shaped. In one embodiment, the 'bottom' of the U-shaped pocket 54 opens up into the fluid distribution manifold 32. In one embodiment, a fluid conduit 55 extends from the bottom of the U-shape and is in fluid communication with the fluid port 46 of the fluid distribution manifold 32. In embodiments, the distal end portion 50 is in fluid communication with the fluid port 46 through two or more individual fluid conduits 55. In one embodiment, the distal end portion 50 is attached to the interior surface 52 by adhering an exterior surface of the distal end portion 50 of the inflatable bladder 40 to the interior surface 52 by providing a suitable adhesive between the surfaces. In other embodiments, the attachment is obtained with weld seams or otherwise done in a welding procedure. Other ways of attaching the distal end portion 50 to the interior surface 52 are acceptable. In one embodiment, the distal end portion 50 includes an annular exterior surface and is attached to the interior surface 52 around an entire periphery of the annular exterior surface of the distal end portion 50. The sectional view of FIG. 5 shows segments 56a-d of the entire peripheral attachment between the annular exterior surface of the distal end portion 50 and the interior surface 52 of the fluid distribution manifold 32. In embodiments, the attachment of the cylinder 22 to the fluid distribution manifold 32 at the distal end 34 of the fluid distribution manifold 32 (FIGS. 1 and 2) is done with similar techniques as described above for the attachment of the inflatable bladder 40 to the fluid distribution manifold 32. In one embodiment, a wall thickness of the inflatable bladder at its attachment to the fluid distribution manifold is similar to a wall thickness of the inflatable cylinder 22 and tapering off to a lesser thickness towards the proximal end of the core. In one embodiment, the wall thickness of the inflatable bladder is uniform over the extent of the inflatable bladder 40. In one embodiment, a length of the inflatable bladder 40 of the base 30 from the proximal end of the fluid distribution manifold to the proximal end of the core 38 in the uninflated state of the bladder is 45 mm or less. In one embodiment, the inflatable bladder can expand in the up to 20 mm in the axial direction.

Still with reference to FIG. 5, in one embodiment, a distal end 57 of the core 38 is received in a groove 59 provided in the proximal end 36 of the fluid distribution manifold 32. Groove 59 is sized to closely fit around and maintain core 38 free from radial movement in relation to a longitudinal axis A-A extending through the base 30. The distal end 57 of the core 38 is not otherwise attached to the groove 59 such that axial movement of the core 38 along axis A-A (see FIG. 6) is allowed.

In one embodiment, the inflatable bladder 40 is attached to the core 38 at a proximal end 58 of the core 38. In one embodiment, the inflatable bladder 40 includes an inner wall 60 and an outer wall 62. In one embodiment, the inner wall 60, but not the outer wall 62, is attached to the proximal end 58 of the core 38. When the inflatable bladder 40 is inflated with inflation fluid, the outer wall 62 moves away from the inner wall 60 as the inflation fluid takes up space between the walls 60, 62 and causes expansion of the inflatable bladder 40 into the inflated state. The inflation causes both radial and axial expansion of the inflatable bladder 40. As such, when the inflatable bladder 40 is inflated, it helps provide a base for a penile implant that is of both increased diameter and increased length. This not only helps provide a stable base for the penile implant, but also has the additional advantage that the surgeon does not have to use and keep stock of penile implant tip extenders of different length, because the base 30 accommodates differently sized anatomies.

The inner wall 60 of the inflatable bladder 40 is attachable to the proximal end 58 of the core 38 by gluing or welding as described above with respect to the attachment of the inflatable bladder to the fluid distribution manifold 32.

In one embodiment, the distal end 57 of the core 38 has the same diameter as the proximal end of the core 38. In one embodiment, the distal end 57 of the core 38 has a larger (wider) diameter than the proximal end of the core 38 and is so configured to provide lateral stability to the core 38 and the base 30.

FIG. 6 illustrates one embodiment of the base 30 in which the inflatable bladder 40 is in an inflated state. In one embodiment, the inflatable bladder 40 is configured to expand both radially in the direction of arrows Y1 and Y2 and axially in the direction of arrow X. In the view of FIG. 6 inflation fluid (not shown) has entered into the inflatable bladder 40 to expand it. As a result, an axial extent L2 of the inflatable bladder 40 in FIG. 6 is longer than an axial extent L1 of the inflatable bladder 40 in FIG. 5, and similarly a radial (or widthwise) extent W2 in FIG. 6 is bigger than W1 in FIG. 5. In one embodiment, radial extent W2 of the inflatable bladder 40 in the inflated state corresponds to a third diameter that is greater than a first diameter D1 of the fluid distribution manifold 32. In embodiments, the radial extent W2 of the inflatable bladder 40 in the inflated state provides an outer surface 42 of the base 30 between the proximal end 58 of the core 38 and the proximal end 36 of the fluid distribution manifold 32 that extends radially beyond an exterior surface 33 of the fluid distribution manifold 32. The view of FIG. 6 illustrates that the core 38 is moved a distance in the proximal direction of arrow X to not fill up an entirety of groove 59. Expansion of the inflatable bladder 40 with inflation fluid to the inflated state causes an axial pull of the core 38 by the inner wall 60 of the inflatable bladder 40 at the proximal end 58 of the core, where the inner wall 60 is attached to the core 38. Configuring the core 38 to move axially helps provide for the base 30 to allow expansion to accommodate larger anatomies while the core 38 additionally provides stability to the base 30 in the crus of the penis. Upon the user's activation, the penile implant may be deflated and return to the state corresponding to the flaccid state of the penis including deflation of the inflatable bladder 40 of the base 30. As the inflatable bladder 40 deflates, core 38 moves axially back to fill up an entirety of the groove 59.

FIG. 7 is a sectional side view of one embodiment of a base 30 wherein the inflatable bladder 40 includes a single outer wall 62 attached to the fluid distribution manifold 32 at the proximal end 36 of the fluid distribution manifold 32. In one embodiment, a distal end portion 50 of the inflatable bladder 40 is attached to the fluid distribution manifold 32 along an entire periphery of the distal end portion 50. In one embodiment, the outer wall 62 of the inflatable bladder 40 is attached to the core 38 at the proximal end 58 of the core. Similar to the embodiments illustrated in FIGS. 5 and 6, one effect of the attachment of a wall of the inflatable bladder 40 to the core 38 is that it provides for the core 38 to follow the movement of the wall of the inflatable bladder during radial and axial expansion of the inflatable bladder and move axially in groove 59.

Figure 8B:
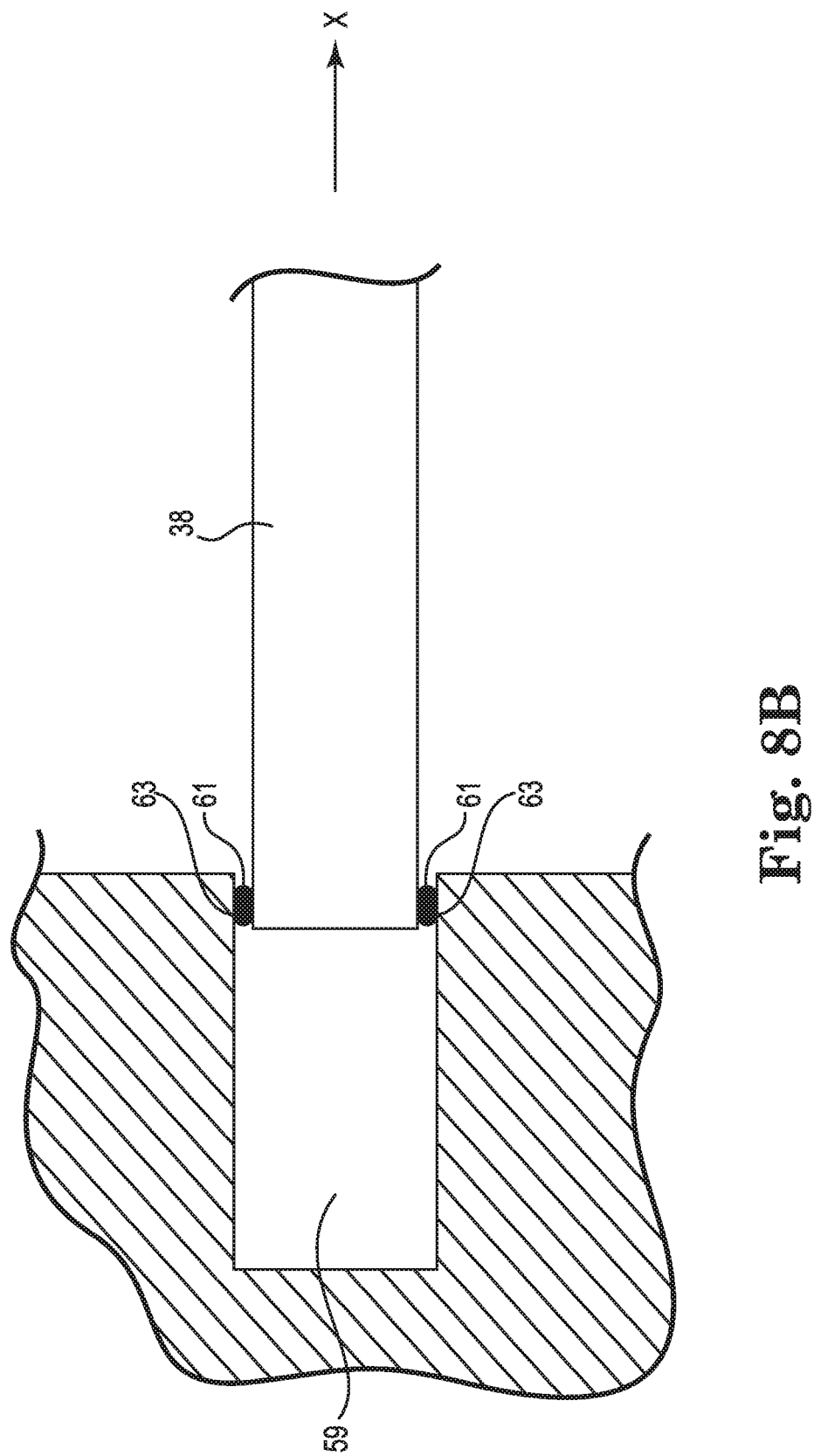

FIGS. 8A and 8B are partial sectional side views detailing the attachment of the core 38 to the fluid distribution manifold 32. In one embodiment, groove 59 includes a stop. In one embodiment, the stop includes one or more protrusions 61 extending from a surface of the groove 59 towards the core 38. In one embodiment, the protrusion extends into the path of the axial movement of the core 38 and is configured to engage with the core 38 to prevent dislocation of the core 38 axially out of the groove 59 in the proximal direction. In one embodiment, the core 38 includes one or more corresponding protrusions 63 configured to engage with the protrusion 61 extending from the surface of the groove 59 to limit or prevent the axial movement of the core 38 out of the groove 59. In one embodiment, the core 38 includes one or more corresponding recesses configured to engage with the protrusion 61 extending from the surface of the groove 59 to limit or prevent the axial movement of the core 38 out of the groove 59. In one embodiment, more than one protrusion 61 extends from a surface of the groove 59.

FIG. 9 is a schematic side view of one embodiment of the fluid distribution manifold 32. The view illustrates a distribution of internal conduits 64, 66, 68, 70 within the fluid distribution manifold 32 according to one embodiment. The internal conduits are configured to guide inflation fluid from the fluid port 46 to the inflatable cylinder 22 (not shown) and to the inflatable bladder 40 (not shown). In one embodiment, the fluid distribution manifold 32 includes a bifurcated fluid conduit 68, 70 configured to guide inflation fluid from a first conduit 64 into the inflatable bladder 40 at the proximal end 36 of the fluid distribution manifold 32. First conduit 64 communicates with a pump and reservoir of the penile prosthetic implant via fluid port 46 and tubing 25 to take in, or send out, inflation fluid during inflation and deflation respectively. In one embodiment, a second conduit 66 guides inflation fluid from the first conduit 64 to the inflatable cylinder 22 attached at the distal end 34 of the fluid distribution manifold 32.

Figure 10:
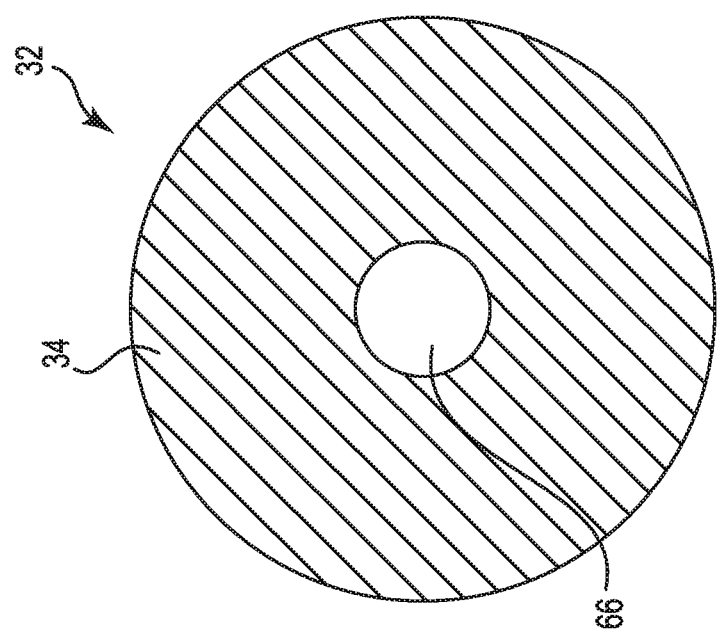
FIG. 10 is a distal end view of one embodiment of a fluid distribution manifold.

FIG. 10 is an end view of the embodiment of the fluid distribution manifold 32 illustrated in FIG. 9 seen from the distal end 34. FIG. 10 illustrates second conduit 66 configured for fluid communication with an inflatable cylinder 22.

Figure 11:
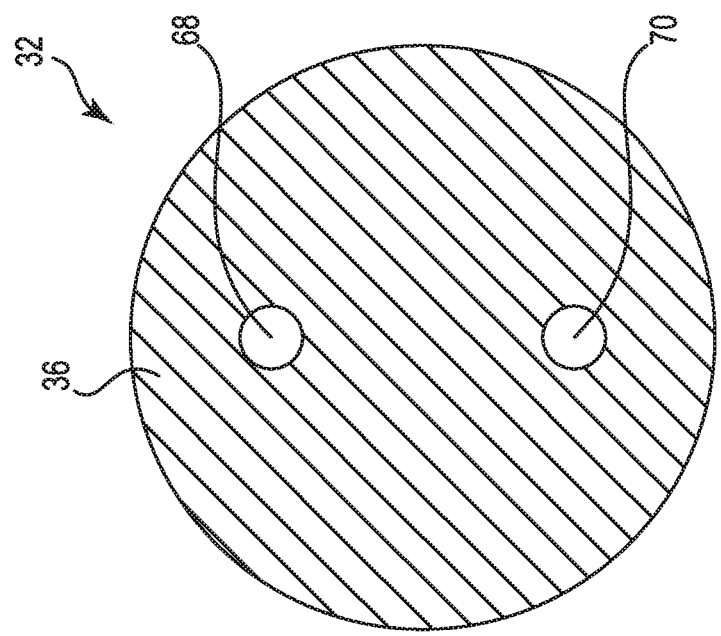
FIG. 11 is a proximal end view of one embodiment of a fluid distribution manifold.

FIG. 11 is an end view of the fluid distribution manifold 32 seen from the proximal end 36 according to one embodiment. FIG. 11 illustrates the bifurcated conduit 68, 70 configured for fluid communication with the inflatable bladder 40. In one embodiment, a cross-sectional area of the second conduit 66 is bigger than a cross-sectional area of each of the individual conduits 68, 70 of the bifurcated conduit.

In other embodiments, the fluid distribution manifold 32 includes a plurality of internal conduits configured to guide inflation fluid to the inflatable cylinder and the inflatable bladder. The number of individual internal conduits for guiding fluid to each of the inflatable cylinder and the inflatable bladder, respectively, can range from 1-8.

Figure 12:
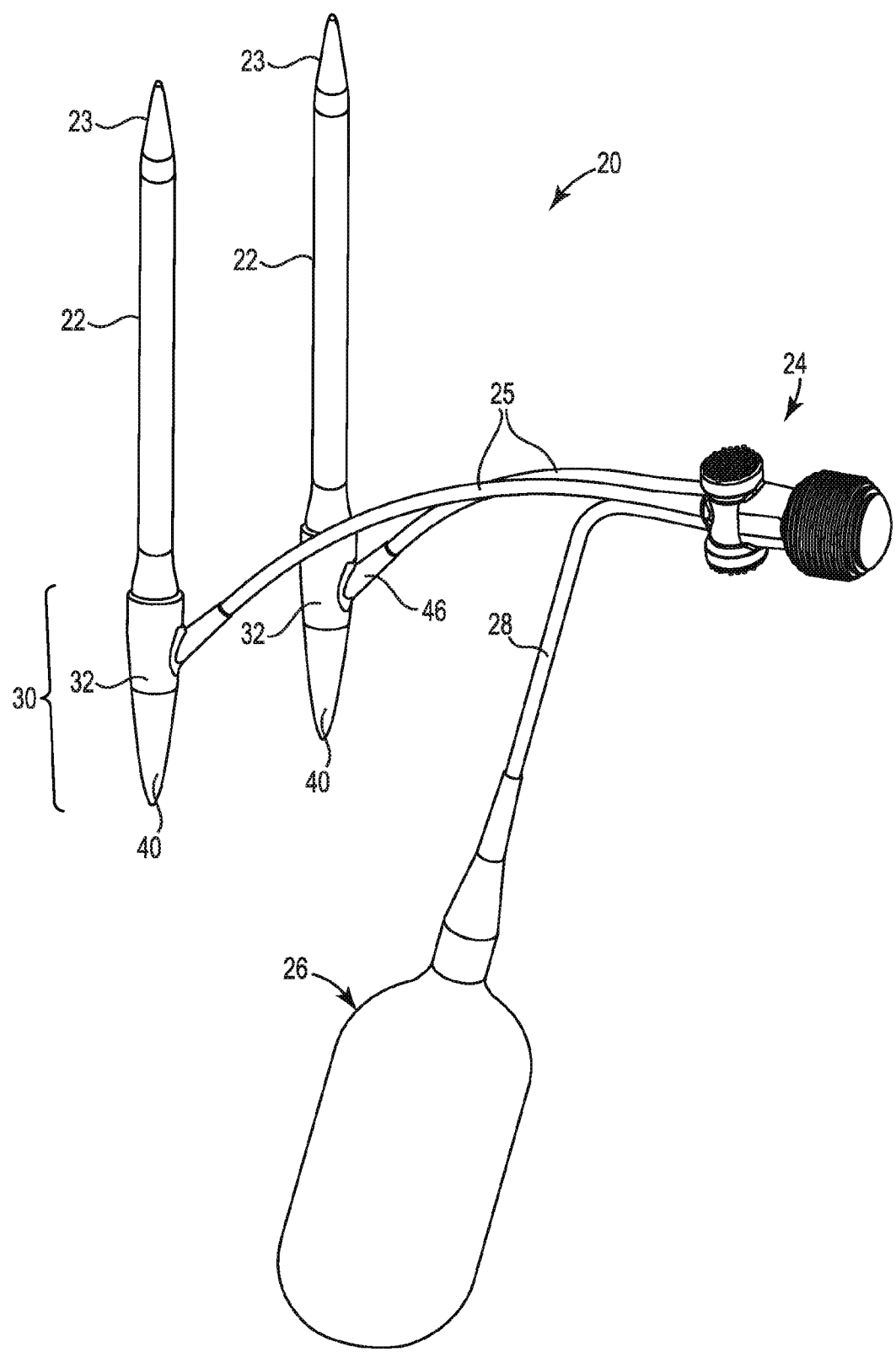
FIG. 12 is a perspective view of one embodiment of a penile prosthetic system.

FIG. 12 is a perspective view of one embodiment of a penile prosthetic system 20 including an inflatable cylinder 22 sized for implantation into a corpora cavernosum of a penis, a pump 24 and a fluid reservoir 26 for storing inflation fluid. The cylinder 22 includes a base 30 in fluid communication with the pump 24 through tubing 25 and the pump 24 in turn is in fluid communication with the fluid reservoir 26 through tubing 28. The base 30 includes a fluid distribution manifold 32 and an inflatable bladder 40. The base 30 also includes fluid port 46 attached to one end of the tubing 25. In one embodiment, the system 20 includes a distal tip 23 attached to a distal end of the cylinder 22. In one embodiment, the penile prosthetic system 20 includes two inflatable cylinders 22.

Suitable materials for fabricating the inflatable cylinder include silicone, polymers such as urethanes, blends of polymers with urethane, copolymers of urethane, or the like. Suitable inflatable cylinders are available from Coloplast Corp., Minneapolis, Minn. In one embodiment, the pump and the reservoir are fabricated from material suitable for body implantation, such as silicone or the urethane-based materials described above for the cylinder.

In embodiments, each of the inflatable bladder, the fluid distribution manifold and the core are suitably fabricated from material suitable for body implantation, such as silicone or the urethane-based materials described above for the cylinder. Other suitable materials for the core include polymers such as polyurethanes, polypropylenes and polysulfones.

Figure 13A:
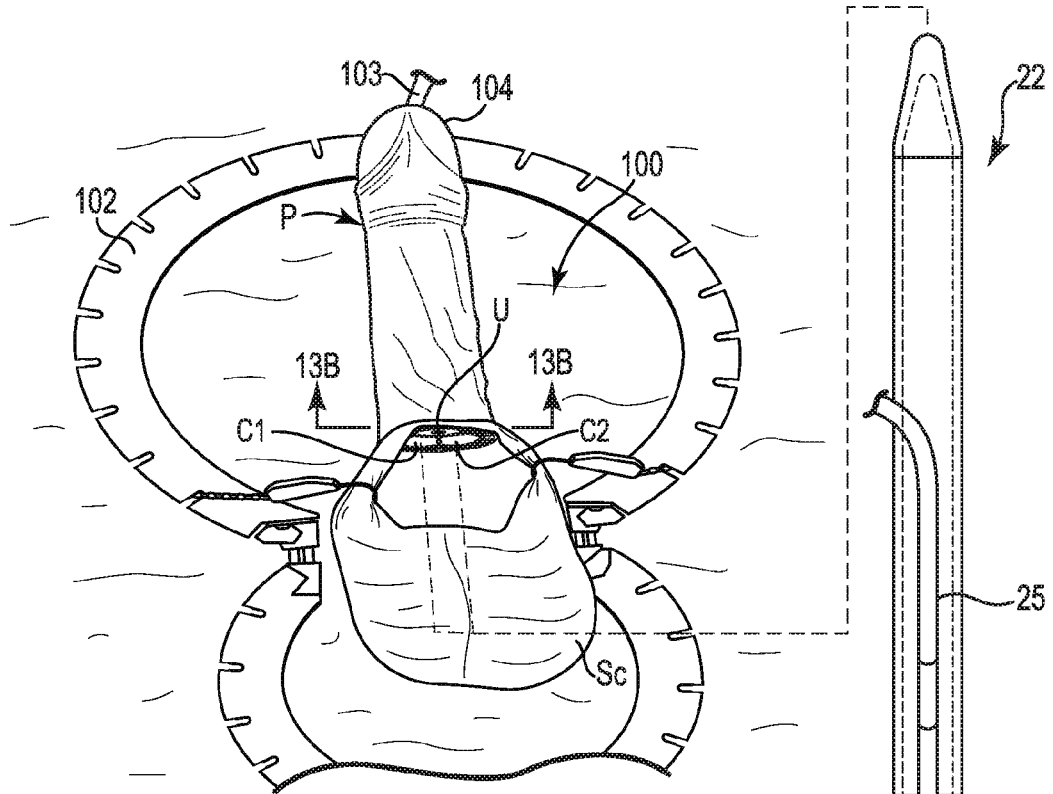
FIG. 13A is a top view and FIG. 13B is a cross-sectional view of a penis prepared to receive a penile implant.
Figure 13B:
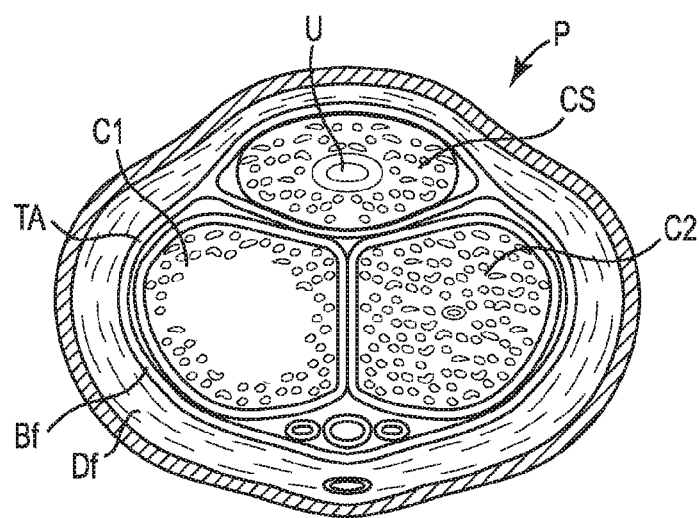

FIG. 13A is a top view and FIG. 13B is a cross-sectional view of a penis P prepared to receive a penile implant 22 having a base 30 including a fluid distribution manifold 32, fluid port 46 and inflatable bladder 40. The corpora cavernosa are illustrated as C1 and C2, where the corpora cavernosum C1 of FIG. 13B has been opened in a corporotomy procedure to a size that is suited to receive penile implant 22. In FIG. 13A a portion of tubing 25 is shown attached to the fluid port 46.

The groin area 100 of the patient is shaved, cleaned and suitably prepped with a surgical solution prior to draping with a sterile drape as directed by the healthcare provider's procedures. A retraction device, such as a retractor 102 sold under the trademark Lone Star and available from Lone Star Medical Products of Stafford, Tex., is placed around the penis P if so desired by the surgeon to establish a surgically clean field. A catheter 103 is inserted into the urethra U from the distal end 104 of the penis P. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum Sc.

As an example of the transverse scrotal approach, with reference to FIG. 13B, the surgeon forms a 2-3 cm transverse incision through the subcutaneous tissue of the median raphe of the upper scrotum Sc and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed through the tissue and the fascia to allow the surgeon to access and subsequently dilate the corpora cavernosa C1 and C2.

In the illustrated example, the penis P is reclined against the torso such that the urethra U, surrounded by corpus spongiosum tissue, is oriented upward. A corporotomy tool, for example a cavernatome (not shown), is introduced into the exposed the corpora cavernosa (C1 and C2 ) to remove (e.g., "core out") the corpora cavernosum C1 proximally and distally. With reference to both FIGS. 13A and 13B, the surgeon typically will insert a blunt-ended scissors or other elongated tool to separate a portion of the spongiosum tissue to open a pathway for the cavernatome. Thereafter, the cavernatome is manipulated within each corpora cavernosum C1 and C2 distally and proximally with sequentially larger diameters until the corporotomy provides an opening of about 10 mm.

A length of the corporotomy is measured from the crus of the penis proximately to a mid-glans location of the penis distally. The surgeon inserts the shaft of the cavernatome into the corporotomy to measure the proximal and distal length of each corpora cavernosum C1 and C2. For example, the shaft is inserted into one of the corpora cavernosa C1 or C2 forward in the distal penis toward the glans penis, the distal measurement is recorded, and the shaft is inserted into the same corpora cavernosum C1 or C2 rearward in the proximal penis toward the crus of the penis to record the proximal length of the corpora. The distal and proximal measurements would typically be made in reference to a "stay stitch" (not shown) temporarily placed in the incision. The sum of the distal and the proximal measurements represent the length of the corporotomy into which the implant 22 is placed. This procedure is repeated for the other of the corpora cavernosa C1 or C2 to measure the length of the companion corpora. Based on the measurements, the surgeon picks a penile implant having a cylinder 22 of a length that best approximates the length of the corporotomy.

Due to the radial and axial expandability of the inflatable bladder 40 of the base 30, and in contrast to non-inflatable bases, the base 30 according to the disclosure is adaptable to a large variety of different anatomies of the crus of the penis while also providing stability of the penile implant in the corpora cavernosum.

Figure 13C:
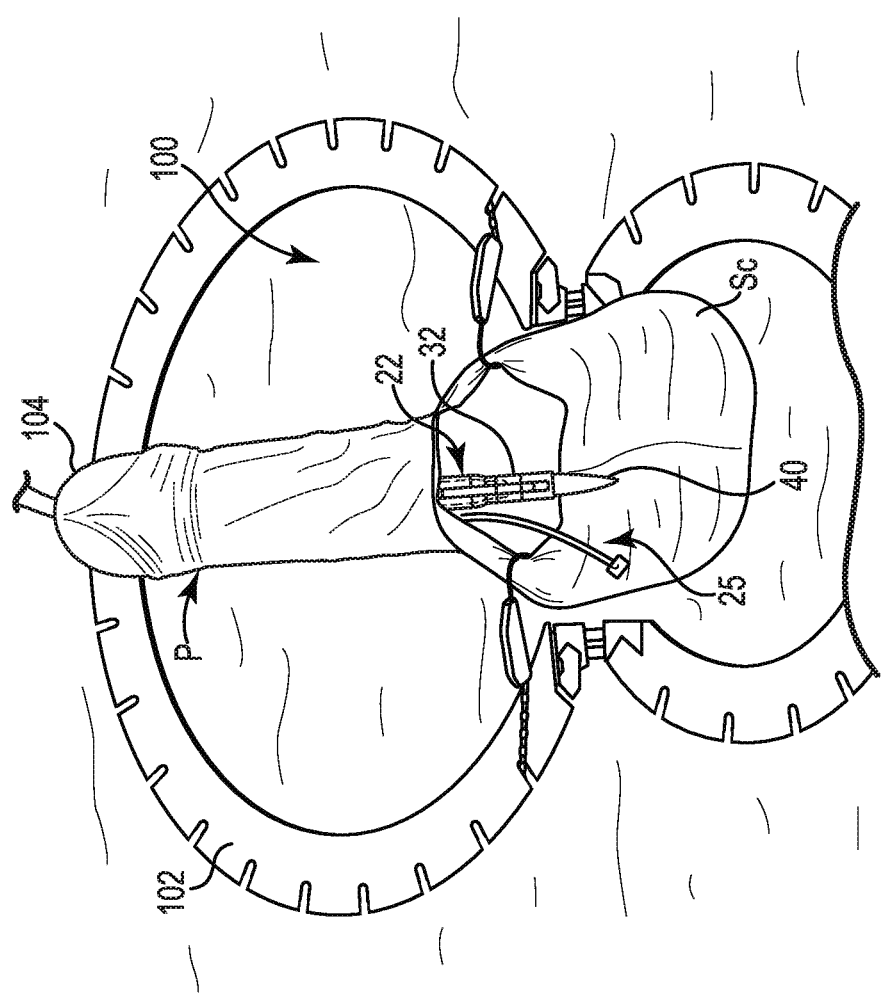
FIG. 13C is a top perspective view of a penile implant with the distal tip implanted into a corporotomy formed in the penis.

As illustrated in FIG. 13C, during implantation of the penile implant 22 into the corpora C1, the inflatable bladder 40 of the base 30 is in a deflated state with a relatively narrow first diameter W1 (see FIG. 5) making it easier to implant and accommodate the base 30 in a patient with a narrower proximal corporotomy.

After insertion of the implant 22 the corporotomy is closed and the remaining portions of the penile prosthetic device, such as the reservoir and/or the pump, are implanted in the abdomen and scrotum S, respectively, of the patient.

Embodiments of a base for a penile prosthetic implant have been disclosed in which the base includes a core and an inflatable bladder that helps provide easier implantation of the base in the crus of a penis and helps provide stability of the implant when it is activated to create an erection.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An implantable penile prosthetic comprising:
 a cylinder sized for implantation into a corpora cavernosum of a penis;
 a base sized for implantation into a crus of the penis; and
 a fluid distribution manifold connected between and in fluid communication with both of the cylinder and the base;
 wherein both of the cylinder and the base have an implantable size and are inflatable with liquid to an expanded size that is larger than the implantable size,
 wherein the fluid distribuion manifold has a tapered outside diameter.

2. The implantable penile prosthetic of claim 1, wherein the base comprises a core and an inflatable bladder connected to the core.

3. The implantable penile prosthetic of claim 1, wherein the base comprises a core and an inflatable bladder connected to the core, and the inflatable bladder provides an outer surface of the base.

4. The implantable penile prosthetic of claim 1, wherein the base comprises a core and an inflatable bladder connected to the core, and the inflatable bladder has two conduits with each of the two conduits in fluid communication with the fluid distribution manifold.

5. The implantable penile prosthetic of claim 1, wherein the base comprises a core and an inflatable bladder connected to the core, and the inflatable bladder is an annular bladder attached around the core.

6. The implantable penile prosthetic of claim 1, wherein the base comprises a core and an inflatable bladder connected to the core, and a distal end portion of the inflatable bladder is attached to an interior surface of the fluid distribution manifold.

7. The implantable penile prosthetic of claim 1, wherein the fluid distribution manifold is cylindrical.

8. The implantable penile prosthetic of claim 1, wherein a fluid port is provided on an exterior surface of the fluid distribution manifold.

9. The implantable penile prosthetic of claim 1, wherein the fluid distribution manifold comprises a bifurcated fluid conduit.

10. An implantable penile prosthetic comprising:
 a cylinder sized for implantation into a corpora cavernosum of a penis;
 a base sized for implantation into a crus of the penis; and
 a fluid distribution manifold connected between and in fluid communication with both of the cylinder and the base, where the fluid distribuion manifold has a tapered outside diameter;
 wherein the implantable penile prosthetic has an implant length extending between a distal end defined by the cylinder and a proximal end defined by the base, and the cylinder and the base are expandable by liquid inflation.

* * * * *